United States Patent
Rachman et al.

(10) Patent No.: US 11,946,278 B2
(45) Date of Patent: Apr. 2, 2024

(54) DEVICE AND SYSTEM UTILIZING ULTRASONIC WAVES IN SPECTROPHOTOMETRICALLY MONITORING THE QUALITY OF WATER IN SWIMMING-POOLS

(71) Applicant: MAYTRONICS LTD., Kibutz Yizrael (IL)

(72) Inventors: Alex Rachman, Holon (IL); Ben Lewis, Herzliya (IL); Shay Peretz, Shimshit (IL)

(73) Assignee: MAYTRONICS LTD., Kibutz Yizrael (IL)

(*) Notice: Subject to any disclaimer, the term of this patent is extended or adjusted under 35 U.S.C. 154(b) by 687 days.

(21) Appl. No.: 17/267,388

(22) PCT Filed: Aug. 6, 2019

(86) PCT No.: PCT/IL2019/050892
§ 371 (c)(1),
(2) Date: Feb. 9, 2021

(87) PCT Pub. No.: WO2020/031183
PCT Pub. Date: Feb. 13, 2020

(65) Prior Publication Data
US 2021/0293043 A1     Sep. 23, 2021

Related U.S. Application Data

(60) Provisional application No. 62/716,638, filed on Aug. 9, 2018.

(51) Int. Cl.
*G01N 21/31*     (2006.01)
*C02F 1/36*      (2023.01)
(Continued)

(52) U.S. Cl.
CPC ............ *E04H 4/1209* (2013.01); *C02F 1/36* (2013.01); *G01F 1/7082* (2013.01); *G01N 21/31* (2013.01);
(Continued)

(58) Field of Classification Search
CPC ............ G01N 21/534; G01N 21/1717; G01N 21/6486; G01N 21/51; G01N 21/31;
(Continued)

(56) References Cited

U.S. PATENT DOCUMENTS 4,961,860 A * 10/1990 Masri .................. B01J 19/10
210/748.03
6,780,306 B2 * 8/2004 Schlager ............. C02F 1/4672
205/466

(Continued)

FOREIGN PATENT DOCUMENTS

CN     1203365 A     12/1998
CN     103230912 A    8/2013
(Continued)

OTHER PUBLICATIONS

Tiffany LL Teo et al., "Chemical contaminants in swimming pools: Occurrence, implications and control", Environment International, Pergamon Press, US, Dec. 11, 2014, pp. 16-31.
(Continued)

*Primary Examiner* — Arlen Soderquist

(57) ABSTRACT

A cuvette for treating and characterizing water via ultrasonic waves and optical measurements comprises at least one ultrasonic transducer for treating said water by introducing at least one ultrasonic pulse into the water. The at least one ultrasonic pulse either varies parameters of the water, and/or moves and repositions particles within the water. The cuvette further comprises a spectrometry device for measuring spectral components of light and at least one light
(Continued)

source for irradiating the water with irradiation light. The at least one of the parameters of the water is determined via: (a) measuring the spectral components of light prior to treating the water with said at least one ultrasonic transducer, (b) treating the water with said at least one ultrasonic transducer, (c) remeasuring the spectral components of light to get the difference in said spectral components of light, and (d) determining the value of the at least one parameter of the water based on the difference in said spectral components of light.

18 Claims, 13 Drawing Sheets

(51) Int. Cl.
    *E04H 4/12*     (2006.01)
    *G01F 1/7082*     (2022.01)
    *G01N 21/53*     (2006.01)
    *G01N 21/64*     (2006.01)

(52) U.S. Cl.
    CPC ....... *G01N 21/534* (2013.01); *G01N 21/6486* (2013.01)

(58) Field of Classification Search
    CPC .......... G01N 33/18; G01N 21/53; B08B 3/12; B08B 3/00; E04H 4/1209
    USPC ........................................ 436/171; 422/82.05
    See application file for complete search history.

(56) References Cited

U.S. PATENT DOCUMENTS

| | | | |
|---|---|---|---|
| 7,808,642 B2 | 10/2010 | Connelly et al. | |
| 8,545,682 B2 | 10/2013 | Jones et al. | |
| 9,776,888 B1 | 10/2017 | Kurani et al. | |
| 2003/0164308 A1* | 9/2003 | Schlager | C02F 1/4672 205/742 |
| 2006/0131245 A1* | 6/2006 | Dennis | C02F 1/008 210/746 |
| 2009/0053688 A1* | 2/2009 | Bystryak | G01N 33/54313 435/7.25 |
| 2017/0248568 A1* | 8/2017 | Yizhack | G01N 21/3577 |
| 2017/0350824 A1* | 12/2017 | Olsen | G01N 21/8507 |
| 2018/0266131 A1* | 9/2018 | Witelson | G01N 33/1826 |
| 2020/0148552 A1* | 5/2020 | Yizhack | C02F 1/008 |

FOREIGN PATENT DOCUMENTS

| | | |
|---|---|---|
| CN | 203275288 U | 11/2013 |
| CN | 204988999 U | 1/2016 |
| JP | 55009746 A * | 1/1980 |
| JP | 2001183360 A | 7/2001 |
| JP | 2004177122 A | 6/2004 |
| KR | 101135697 B1 | 4/2012 |
| WOn | 2017046808 A1 | 3/2017 |

OTHER PUBLICATIONS

I.N. Martyanov et al: "Influence of solution composition and ultrasonic treatment on optical spectra of TiO2 aqueous suspensions" Journal of colloid and interface science, academic press Inc. US, 267(1):111-116 (Nov. 1, 2003).

Jong Ho Lee et al: "The preparation of TiO2 nanometer photocatalyst film by a hudrothermal method and its sterilization performance for Giardia lamblia", Water research, Elsevier, Amsterdam, NL, 38(3):713-719 (Feb. 1, 2004).

* cited by examiner

Training modules 9064

| Acquiring the value of a parameter in the tested liquid (such as, for instance, pH) in an initial measurement [9100]    90640 |

| Acquiring light measures in the tested liquid (such as absorbance for determining the pH) prior to generating at least one ultrasonic wave [9200]    90644 |

| generating at least one ultrasonic wave characterized by an amplitude and frequency suitable for varying the parameter pH in the liquid by module [9300]    90646 |

| Acquiring of absorbance measurements at the end of the generated at least one ultrasonic wave [9400]    90648 |

| Acquiring the value of the parameters (such as pH) at the end of the generated at least one ultrasonic wave [9500]    90650 |

| Creating a learning model, such as a chemometric model, for each one of the parameters for determining the values of the parameters [9600]    90652 |

Fig. 10

Testing modules 9084

Acquiring light characteristic in the tested liquid (such as absorbance for determining the pH) prior to generating at least one ultrasonic wave [9700]   90842

Generating at least one ultrasonic wave characterized by an amplitude and frequency suitable for varying the parameter (such as pH) in the liquid by module [9800]   90844

Acquiring light characteristic in the tested liquid (such as absorbance for determining the pH) at the end of at least one ultrasonic wave [9900]   90846

Applying Learning Model 9066 and determining the value of the parameter (such as pH) [9950]   90848

Fig. 11

DEVICE AND SYSTEM UTILIZING ULTRASONIC WAVES IN SPECTROPHOTOMETRICALLY MONITORING THE QUALITY OF WATER IN SWIMMING-POOLS

FIELD OF THE INVENTION

The present invention relates to the field of water quality monitoring. More specifically, the present invention relates to automated monitoring the quality of water in swimming-pools.

BACKGROUND OF THE INVENTION

Swimming pools are basically public bath tubs that become highly contaminated when crowded. Users transfer sweat, dirt, oils, and sunscreen into the pool water, impacting pool chemistry while other contaminants such as insects and leaves emerge from the surroundings. Therefore, effective swimming pool water quality monitoring and control systems are highly essential to keep water clean and safe.

Thus, an aim of the present invention is to provide a system and method for monitoring the quality of liquid in general and specifically the quality of water in swimming-pools.

SUMMARY OF THE INVENTION

In accordance with some embodiments there is thus provided a cuvette for treating and characterizing water via at least one ultrasonic wave and optical measurements. The cuvette comprises:
- at least one ultrasonic transducer for treating the water by introducing at least one ultrasonic wave into the water, the at least one ultrasonic wave either varies parameters of the water, and/or moves and repositions particles within the water,
- a spectrometry device for measuring spectral components of light, and
- at least one light source for irradiating said water with irradiation light,
  - wherein at least one of said parameters of the water is determined via:
  - (a) measuring the spectral components of light prior to treating the water with said at least one ultrasonic wave;
  - (b) treating the water with said at least one ultrasonic wave;
  - (c) remeasuring the spectral components of light to get the difference in said spectral components of light, and
  - (d) determining the value of the at least one parameter of the water based on the difference in said spectral components of light.

Furthermore, in accordance with some embodiments of the present invention, the at least one light source is arranged at a 90-degree angle to the spectrometry device, and/or at a 180-degree angle to the spectrometry device.

Furthermore, in accordance with some embodiments of the present invention, the at least one transducer is at least one low frequency ultrasonic transducer and/or at least one spherical transducer.

Furthermore, in accordance with some embodiments of the present invention, the at least one ultrasonic transducer generates at least one ultrasonic wave characterized by an amplitude and frequency suitable for varying each one of said at least one parameter or for moving and repositioning particles within the water.

Furthermore, in accordance with some embodiments of the present invention, the at least one parameter is selected from pH, free chlorine, combined chlorine, calcium/Magnesium/Total Hardness, bacteria, flow rate, and temperature.

Furthermore, in accordance with some embodiments of the present invention, each one of the at least one ultrasonic transducers is connected to a pulser/receiver and/or pulse generator.

Furthermore, in accordance with some embodiments of the present invention, each one of the at least one ultrasonic transducers comprises a sensor having a frequency range of 20-120 KHZ.

Furthermore, in accordance with some embodiments of the present invention, repositioning particles within the water is influenced by (a) the frequency of the ultrasound waves, (b) the time required to center the particles along an optical measurement axis, and (c) the intensity and frequency of the ultrasound wave(s).

Furthermore, in accordance with some embodiments of the present invention, there is also provided a cuvette-based system for treating and characterizing water via at least one ultrasonic wave and optical measurements, and for monitoring, analyzing and determining of parameters in water. The cuvete-based system comprises: the above-described cuvette,
a processing unit accumulating data from the cuvette, and
an online server, the online server receiving the data from the processing unit, applying machine learning algorithms to incorporate said data and providing values of measured parameters of said water,
wherein the machine learning algorithms comprising at least one learning model trained to learn the behavior of the data acquired from the cuvette and to provide values of parameters of the water.

Furthermore, in accordance with some embodiments of the present invention, the parameters are selected from pH, concentration of free chlorine, concentration of combined chlorine, concentration of bacteria, Calcium/Magnesium/Total Hardness concentration, flow rate and temperature.

Furthermore, in accordance with some embodiments of the present invention, either one of the pH, the concentration of free chlorine, and the concentration of combined chlorine is determined via the difference in the absorbance of light in the water.

Furthermore, in accordance with some embodiments of the present invention, the total hardness in the water is determined via the difference in the reflectance/turbidity of light in the water.

Furthermore, in accordance with some embodiments of the present invention, the concentration of bacteria in the water is determined via the difference in the fluorescence of light.

Furthermore, in accordance with some embodiments of the present invention, the processing unit accumulating at least one of the following data:
  pH measurements prior to and after treating the water with at least one ultrasonic wave,
  free chlorine measurements prior to and after treating the water with at least one ultrasonic wave,
  combined chlorine measurements prior to and after treating the water with at least one ultrasonic wave,
  calcium/magnesium/total hardness concentration measurements prior to and after treating the water with at least one ultrasonic wave, bacteria measurements prior to and after treating the water with at least one ultrasonic wave, flow rate measurements prior to and after treating the water with at least one ultrasonic wave, temperature measurements prior to and after treating the water with at least one ultrasonic wave, and the time of day, day of week and month of the year at which each one of said measurements are conducted.

Furthermore, in accordance with some embodiments of the present invention, each one of the at least one learning model is trained to provide a value of one of the parameters.

Furthermore, in accordance with some embodiments of the present invention, the cuvette-based system further comprising:

a liquid splitter,
a De-bubbler system,
a cooling system, and
a liquid combiner, wherein when said water enters said cuvette-based system, it passes into said liquid splitter where it splits into two streams, a first stream and a second stream, the first stream enters into said cooling system for cooling multiple components of said cuvette-based system, and the second stream enters into said De-bubbler to remove bubbles from the water prior to entering into said cuvette, the water exiting from said cuvette recombines with the water exiting from said cooling system in said liquid combiner.

Furthermore, in accordance with some embodiments of the present invention, the first stream enters into said cooling system for cooling at least one of the first light source, the second light source, and the spectrometer.

Furthermore, in accordance with some embodiments of the present invention, there is also provided a method for treating and characterizing water via at least one ultrasonic wave and optical measurements, and for monitoring, analyzing and determining of parameters in water. The method comprising:

(a) providing the above cuvette-based system;
(b) measuring the spectral components of light prior to treating the water with said at least one ultrasonic wave;
(c) treating the water with said at least one ultrasonic wave;
(d) remeasuring the spectral components of light to get the difference in said spectral components of light, and
(e) determining the value of the at least one parameter of the water based on the difference in said spectral components of light,
(f) accumulating data from said cuvette, and
(g) using machine learning algorithms comprised of a learning model trained to learn the behavior of said data acquired from said cuvette and to provide values of parameters of said water.

Furthermore, in accordance with some embodiments of the present invention, the at least one parameter is selected from pH, concentration of free chlorine, concentration of combined chlorine, concentration of bacteria, Calcium/Magnesium/Total Hardness concentration, flow rate and temperature.

Furthermore, in accordance with some embodiments of the present invention, the above method comprising determining any one of the pH, the concentration of free chlorine, and the concentration of combined chlorine via the difference in the absorbance of light in the water.

Furthermore, in accordance with some embodiments of the present invention, the above method comprising determining the total hardness in the water via the difference in the reflectance/turbidity of light in the water.

Furthermore, in accordance with some embodiments of the present invention, the above method comprising determining the concentration of bacteria in the water via the difference in the fluorescence of light.

BRIEF DESCRIPTION OF THE FIGURES

FIG. 10 is a flow diagram depicting the functionality of training modules according to some embodiments of the present invention.

FIG. 11 is a flow diagram depicting the functionality of testing modules according to some embodiments of the present invention.

DETAILED DESCRIPTION OF THE INVENTION

Figure 1:
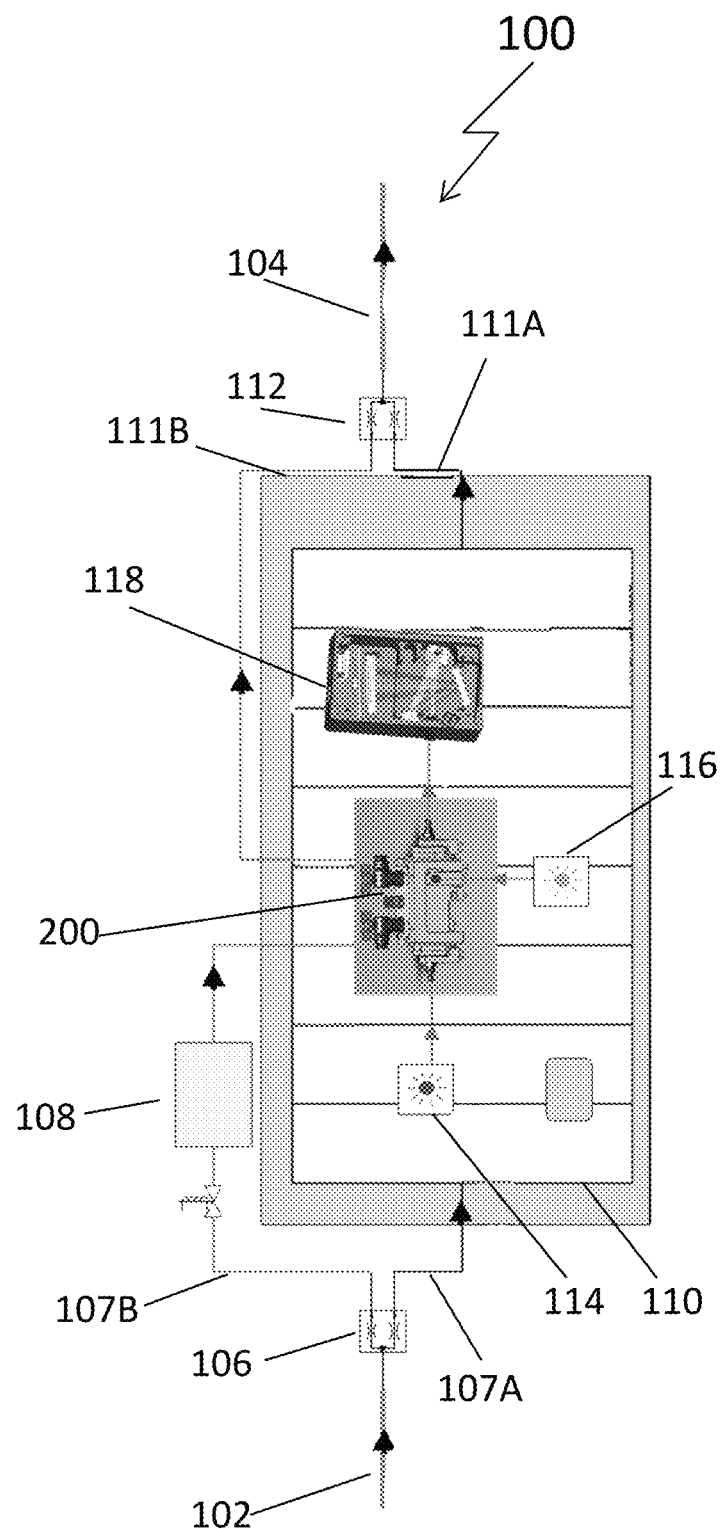
FIG. 1 illustrates a schematic block diagram of a cuvette-based system used for treating and characterizing water via ultrasonic waves and optical measurements respectively in accordance with some embodiments of the present invention.

FIG. 1 illustrates a schematic block diagram of a cuvette-based system 100 used for treating and characterizing water via ultrasonic waves and optical measurements respectively in accordance with some embodiments of the present invention.

Seen in the figure, cuvette-based system 100 comprises a cuvette 200 with at least one ultrasonic transducer (not shown in the figure) for generating acoustic waves, water inlet 102, water outlet 104, liquid splitter 106, De-bubbler system 108, cooling system 110, liquid combiner 112, first light source 114, second light source 116, and spectrometer 118 for measuring various parameters in the water medium and outputting spectral measurements prior to and after treating the water medium with ultrasonic waves.

In accordance with some embodiments of the present invention, a stream of water enters cuvette-based system 100 through water inlet 102 and passes into liquid splitter 106 where it splits into two streams, streams 107A&B. Stream 107A enters cooling system 110 for cooling various components of cuvette-based system 100 such as first light source 114, second light source 116, and spectrometer 118. Stream 107B enters into De-bubbler 108 to remove bubbles from the water prior to entering into cuvette 200. The stream of water, stream 111B, exiting from cuvette 200 recombines in water combiner 112 with the stream of water exiting from cooling system 110, stream 111A.

In accordance with some embodiments of the present invention, a light beam generated via either the first light source 114 or the second light source 116 is directed to cuvette 200 and to spectrometer 118.

In accordance with some embodiments of the present invention, cuvette 200 may have various configurations some of which are described below.

Figure 2:
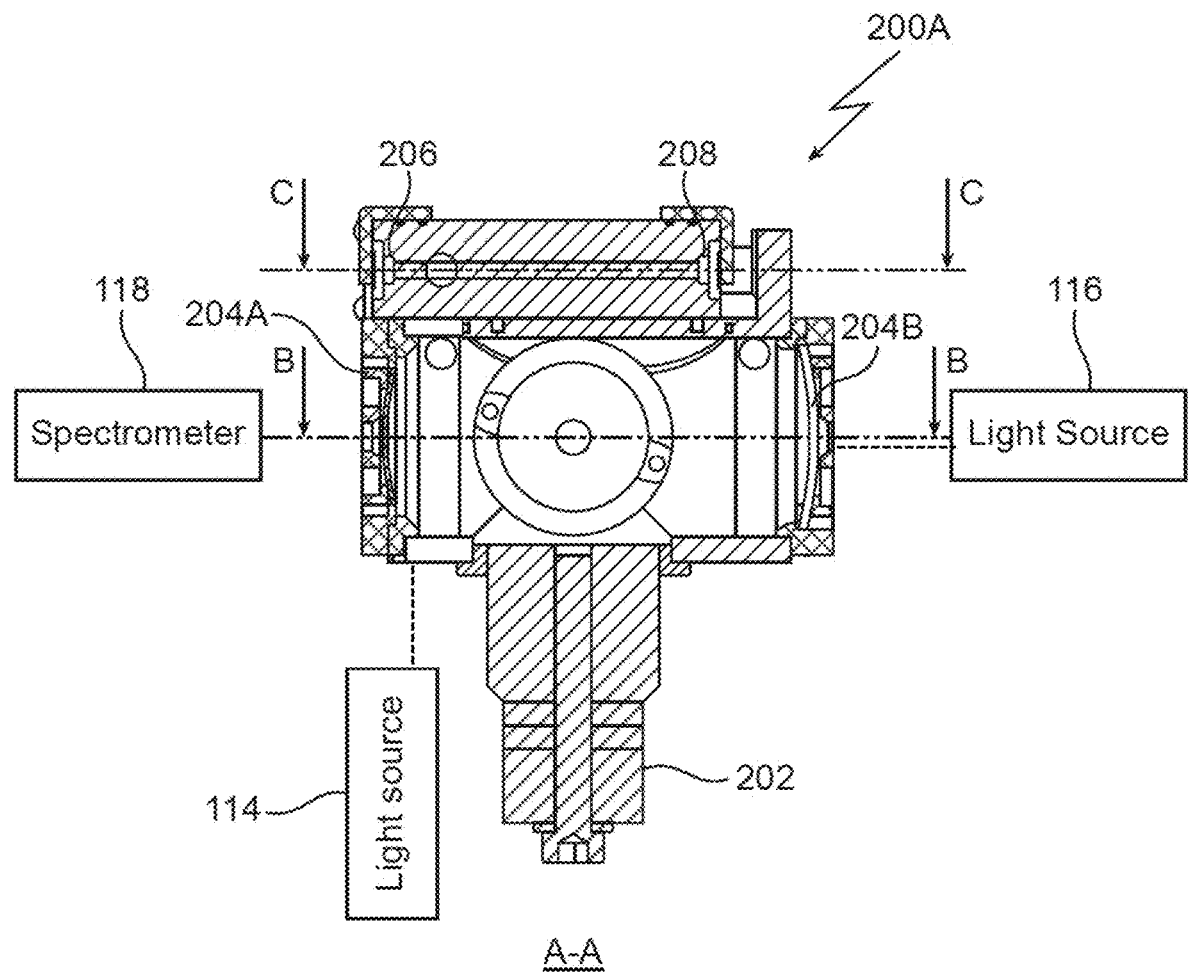
FIG. 2 illustrates a cross sectional view of a cuvette in accordance with some embodiments of the present invention.

FIG. 2 illustrates a cross sectional view of cuvette 200A in accordance with some embodiments of the present invention. Seen in the figure, cuvette 200A comprises a low frequency ultrasonic transducer 202 intended, inter alia, to (a) clean optical lenses in cuvette 200A, (b) vary multiple parameters in the water medium, and (c) move and reposition particles within the water medium as explained in detail below. Cuvette 200A further comprises spherical transducers 204A&B intended, inter alia, to clean optical lenses in cuvette 200A.

In accordance with some embodiments of the present invention, each one of low frequency ultrasonic transducer 202 and spherical transducers 204A&B is connected to an electronic generator (not seen in the figure).

Cuvette 200A further comprises a first light source 114, a second light source 116 and a spectrometer 118 for measuring the spectral components of light prior to and after treating the water with at least one of transducers 202 and 204A&B.

Also seen in FIG. 2 are ultrasonic transducer 206 and ultrasonic transducer 208 used for measuring multiple parameters such as temperature and flow rate of water.

Each of ultrasonic transducers 206 & 208 is connected to a pulser/receiver (not shown in the figure).

Figure 3:
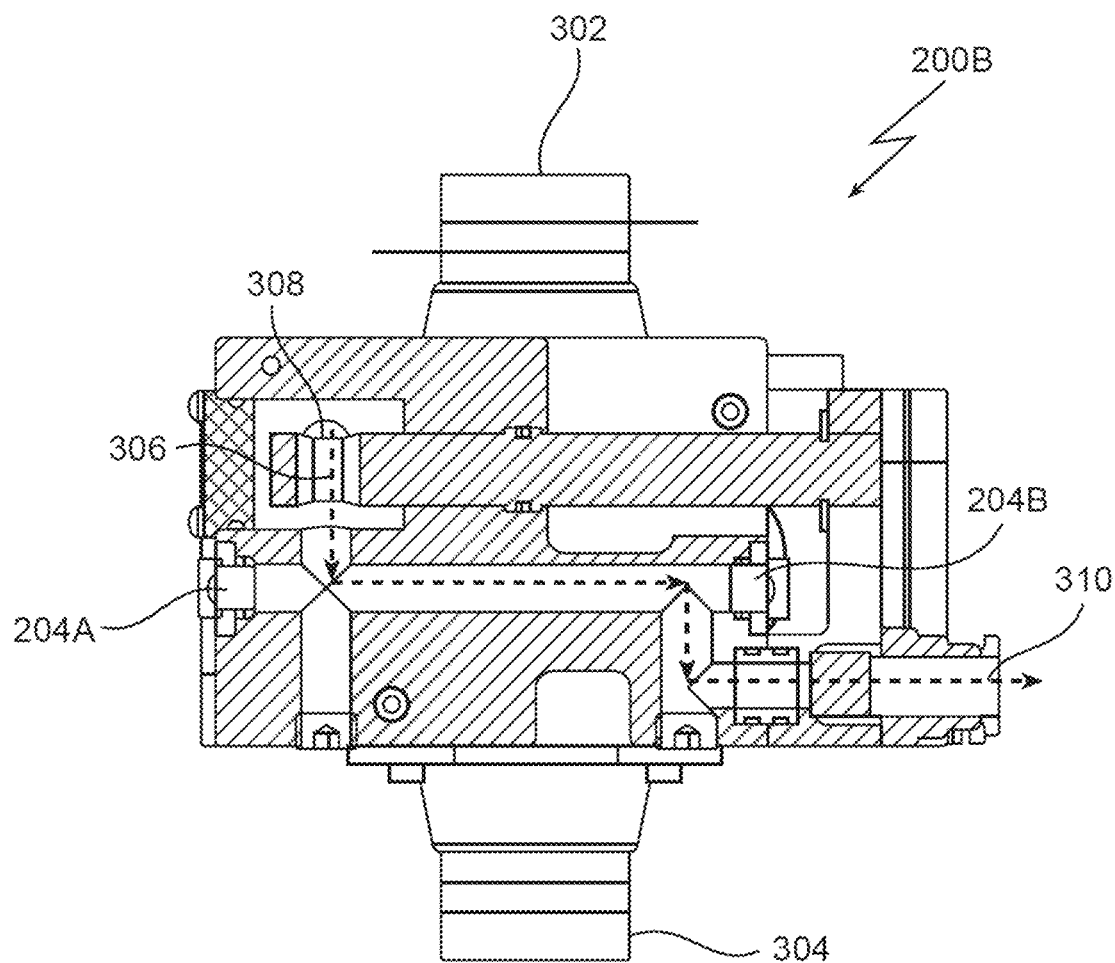
FIG. 3 illustrates a cross sectional view of another cuvette in accordance with some embodiments of the present invention.

FIG. 3 illustrates a cross sectional view of cuvette 200B in accordance with some embodiments of the present invention. Seen in the figure, cuvette 200B comprises two low frequency transducers, first low frequency ultrasonic transducer 302 and second low frequency ultrasonic transducer 304 intended, inter alia, to (a) clean optical lenses in cuvette 200B, (b) vary multiple parameters in the water medium, and (c) move and reposition particles within the water medium as explained in detail below.

Cuvette 200B may further comprise spherical ultrasonic transducers 204A&B intended, inter alia, to clean optical lenses in cuvette 200B.

Low frequency transducers 204A&B, 302 and 304 are connected to a generator and comprise a low frequency sensor with a frequency range of 20-120 KHZ and up to 50 watt. In addition, cuvette 200B comprises at least one light source and a spectrometer (not seen in the figure) for measuring the spectral components of light prior to and after treating the water with at least one of the transducers described above.

Additionally, cuvette 200B may comprise multiple ultrasonic transducers for measuring multiple parameters such as temperature and flow rate of water in the cuvette.

Also seen in the figure is the flow path of water 306 entering and exiting cuvette 200B at entrance and exit points 308 and 310 respectively.

Figure 4:
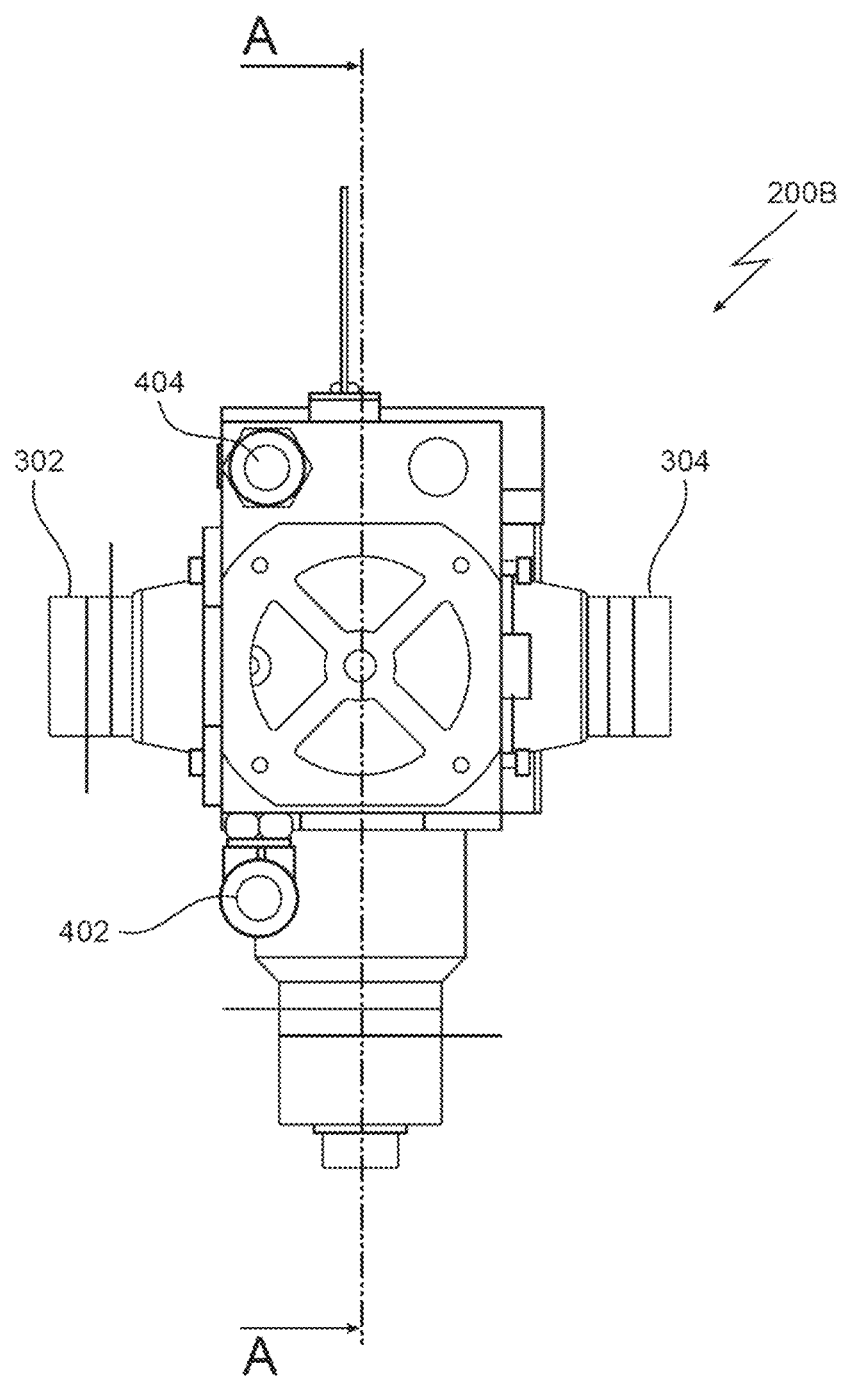
FIG. 4 is a top view of the cuvette of FIG. 3.

FIG. 4 is a top view of cuvette 200B shown in FIG. 3. Seen in the figure are first low frequency transducer 302 and second low frequency transducer 304 as well as water inlet valve assembly 402 and water outlet valve assembly 404.

Cleaning the Cuvette

In accordance with some embodiments of the present invention, the acoustic cavitation phenomenon may be used for cleaning cuvette 200.

Acoustic cavitation is a term used to describe the influence of an ultrasonic wave on the formation, growth, oscillation and collapse of bubbles (gaseous cavities) in a water medium. A sound wave propagating through water, consists of expansion (negative-pressure) and compression (positive-pressure) half cycles. If the pressure in the sound wave is high enough, in the expansion half-cycles, the distance between water molecules can exceed the critical molecular distance necessary to hold the water intact. Consequently, the water may break down and bubbles (gas-filled cavities) will be created. As the pressure of the ultrasound wave increases, bubbles experience rapid growth following by a collapse. This phenomenon is called inertial or transient cavitation, and it is characterized by shock waves formation in the bulk of the water, or micro-jets near a boundary. These micro jets at the boundary water-glass clean the lenses.

In accordance with some embodiments of the present invention, the acoustic cavitation phenomenon, e.g., formation, growth and collapse of bubbles is accompanied by generation of local high temperature, pressure, and reactive radical species (° OH, ° OOH) by thermal dissociation of water and oxygen. These radical species penetrate into water and oxidize dissolved organic compounds, and thus, clean the surface from various pollutants and prevent pollutants from accumulating on the surface.

Thus, in accordance with some embodiments of the present invention, acoustic cavitation may be induced by at least one ultrasound transducer.

Figure 5:
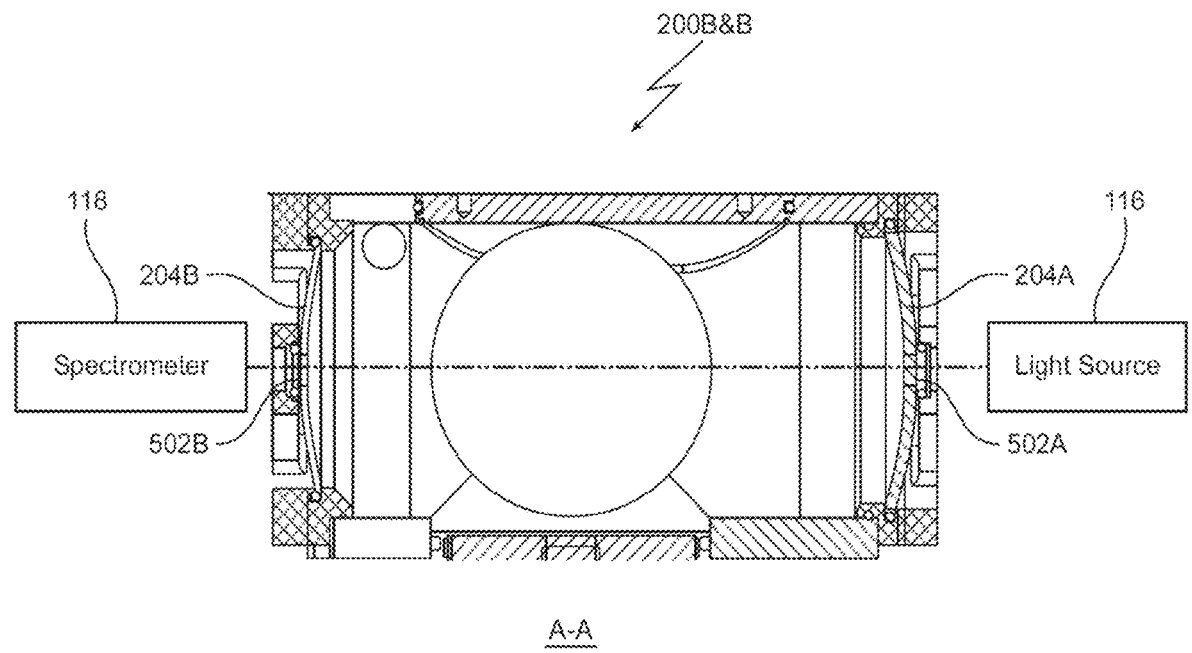
FIG. 5 illustrates a top view of a section of the cuvettes of FIGS. 2 & 3 in accordance with some embodiments of the present invention.

FIG. 5 illustrates a top view of a section of cuvette 200A and cuvette 200B in accordance with some embodiments of the present invention. Seen in the figure are concave spherical transducers 204A&B, light source 116, and spectrometer 118.

Ultrasonic transducers 204A&B are configured to propagate ultrasonic waves across exposed surfaces of cuvette 200A and cuvette 200B, and to concentrate cavitation cleaning of the cuvette at points of optical path entry and exit from the cuvette, i.e., at optical lenses 502A&B, i.e., transducer 204A is configured to propagate ultrasonic waves across exposed lens 502B and transducer 204B is configured to propagate ultrasonic waves across exposed lens 502A.

Transducers 204A&B should be tuned to generate acoustic waves with a maximum possible intensity focused at a desired point/section on lenses 502A and 502B for cleaning purposes. However, to avoid scratching and damaging the treated lens and/or other optical components in the cuvette, the frequency and the strength of transducers 204A&B should be tuned correspondingly.

In accordance with some embodiments of the present invention, changes in a reflectance/turbidity spectrum are measured to detect the onset of cavitation, its duration, and intensity in the aqueous media in the cuvette and to determine ultrasonic application parameters (e.g. frequency, power amplitude, etc.) leading to cavitation so as not to otherwise interfere with optical measurements.

Figure 6:
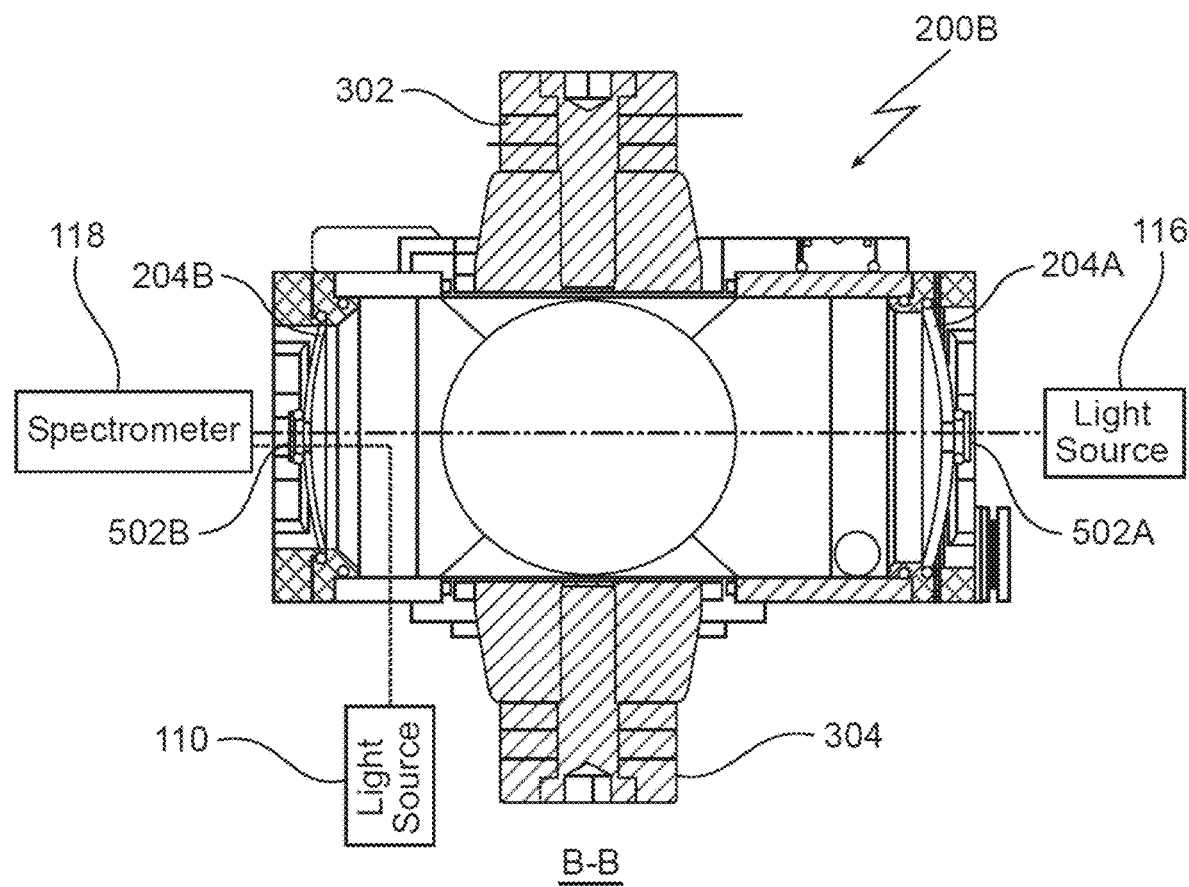
FIG. 6 illustrates a cross-sectional view of the cuvette of FIG. 3.

FIG. 6 illustrates a cross-sectional view of cuvette 200B. Seen in the figure are spherical transducers 204A&B having a concave spherical shape. Transducers 204A&B may be configured to propagate ultrasonic waves across exposed surfaces of cuvette 200B and to concentrate cavitation cleaning of optical lenses 502A&B. Also seen in the figure are low frequency transducers 302 and 304.

In accordance with some embodiments of the present invention, transducer 204A is configured to propagate ultrasonic waves across exposed lens 502B and transducer 204B is configured to propagate ultrasonic waves across exposed lens 502A.

Transducers 204A&B may be tuned to generate acoustic waves with a maximum possible intensity focused at a desired point/section on lenses 502A&B for cleaning lenses 502A&B. However, to avoid scratching and damaging the treated lens and/or other optical components in the cuvette, the frequency and the strength of transducers 204A&B should be tuned correspondingly.

In accordance with some embodiments of the present invention, at least one of ultrasonic transducers 302 and 304 is used to superimpose with ultrasonic transducers 204A&B during cavitation cleaning to further control the focus of cavitation cleaning of the cuvette at points of optical path entry and exit from the cuvette.

Temperature Measurements

In accordance with some embodiments of the present invention, the temperature of the water medium in cuvette 200A and/or 200B may be determined via ultrasonic transducers 206& 208 seen in FIG. 2 and transducers 204A&B seen in FIGS. 2 and 3.

Transducers 206&208 and transducers 204A&B enable speed measurements by measuring time-of-flight of an acoustic pulse in standing water. In accordance with some embodiments of the present invention, ultrasonic transducers 206 and 208 are used as a transmitter and receiver to generate and detect acoustic waves in standing water in cuvette 200A.

To examine the accuracy of the measurement, the measurement is repeated the other way around—with ultrasonic transducer 208 acting as a transmitter and ultrasonic transducer 206 as a receiver. Then, a plot correlating the temperature and the speed of sound in water is used for determining the temperature of the water media by correlating the measured speed of sound and the corresponding temperature.

It should be noted that when the water temperature is as low as 4° C., the pool is being emptied automatically to prevent the pool from getting damaged.

Flow Rate Measurements

In accordance with some embodiments of the present invention, ultrasonic transducers 206 and 208 seen in FIG. 2 and transducers 204A&B seen in FIGS. 2 & 3 may be used for measuring the speed of sound in water to determine flow parameters such as volumetric flow rate.

In accordance with some embodiments of the present invention, flow rate measurements are conducted while liquid is flowing in and out of cuvette 200, and ultrasound transducers 206 & 208 (or transducers 204A&B) are used as a transmitter and a receiver to generate and detect acoustic waves traveling in both directions, e.g., in the direction and against the direction of the water flow.

To determine the flow rate of water in cuvette 200 the following procedure is carried out:

Acoustic transducer 208 generates acoustic waves with a specific frequency in the direction of the water flow, ultrasonic transducer 206 detects such propagating waves and transfers a corresponding electric signal to an electronic circuitry (not seen in the figure) based on which the electronic circuitry determines time-of-flight and calculates the sound velocity.

Acoustic transducer 206 generates acoustic waves with a specific frequency in a direction opposite to the direction of water flow, ultrasonic transducer 208 detects such propagating waves and transfers a corresponding electric signal to an electronic circuitry (not seen in the figure) based on which the electronic circuitry determines time-of-flight and calculates the sound velocity.

The flow rate of water is retrieved from the average of these two measurements, i.e., from the average sound velocity of waves propagating in and against the direction of flow.

In accordance with some embodiments of the present invention, prior to the flow rate measurements, acoustic transducers 206 and 208 may be calibrated by an external reference system—the water flow rate measured by acoustic transducers 206 and 208 in cuvette 200 may be compared to and calibrated based on water flow rate measurements carried out by an external reference system.

Varying Multiple Water Parameters Via Ultrasound Waves pH

Ultrasound waves can vary the pH as well as other parameters of the water. In accordance with some embodiments of the present invention, ultrasonic waves may be used to vary the pH of the water in cuvette 200A and cuvette 200B.

In accordance with some embodiments of the present invention, at least one of transducers 204A&B (or 302&304) generates ultrasonic waves characterized by an amplitude and frequency suitable for varying the water pH, and spectrometer 118 is used for measuring the pH of the water after the acoustic irradiation.

In accordance with some embodiments of the present invention, the pH of the water may be determined as follows:

the absorbance of the water is measured prior to the application of ultrasonic wave;

at least one ultrasonic wave is applied to the water;

the absorbance of the water is remeasured after the application of the ultrasonic wave(s); and the difference in the absorbance is used for determining the pH of the water and for examining the effect of ultrasound wave(s) on the pH.

Free Chlorine

The absorbance spectrum of free chlorine varies characteristically according to the concentration of free chlorine and the pH of the water.

In accordance with some embodiments of the present invention, ultrasonic wave(s) characterized by an amplitude and frequency suitable for varying the pH of the water may be generated via transducers 204A&B to vary the concentration of free chlorine in water.

Thus, in accordance with some embodiments of the present invention, the concentration of free chlorine in the water may be determined as follows:

the absorbance of the water is measured prior to the application of ultrasonic wave;

at least one ultrasonic wave is applied to the water to vary the pH of the water;

the absorbance of the water is remeasured after the application of the ultrasonic wave(s); and the difference in the absorbance is used for determining the concentration of free chlorine in the water.

Combined Chlorine

Ultrasonic waves are suitable for removing or for reducing the amount of combined chlorine in the water. Thus, in accordance with some embodiments of the present invention, at least one of the transducers in cuvettes 200A and 200B, e.g., at least one of transducers 204A&B, 302 and 304 generates ultrasonic wave(s) characterized by an amplitude and frequency suitable for reducing the concentration of combined chlorine in the water medium, and spectrometer 118 is used for measuring the concentration of the combined chlorine in the water medium prior to and at the end of the acoustic treatment.

Thus, in accordance with some embodiments of the present invention, the concentration of combined chlorine in the water may be determined as follows:

the absorbance of the water is measured prior to the application of ultrasonic wave;

at least one ultrasonic wave is applied to the water;

the absorbance of the water is measured after the application of the ultrasonic wave(s); and the difference in the absorbance is used for determining the concentration of combined chlorine in the water.

Calcium/Magnesium/Total Hardness

In accordance with some embodiments of the present invention, ultrasonic waves may be used to reduce the Calcium/Magnesium/Total Hardness concentration of water. The removal rate of such impurities depends on the amplitude and frequency of the ultrasonic waves and proceeds by a characteristic increase in the turbidity intensity level.

In accordance with some embodiments of the present invention, at least one of the transducers in cuvettes 200A and 200B, i.e., at least one of transducers 204A&B, 302 and 304 generates ultrasonic waves characterized by an amplitude and frequency suitable for reducing the Calcium/Magnesium/Total Hardness concentration of water, and spectrometer 118 is used for measuring changes in the turbidity intensity level.

Thus, in accordance with some embodiments of the present invention, the concentration of the Calcium/Magnesium/Total Hardness in the water may be determined as follows:

the turbidity in the water is measured via reflectance measurements prior to the application of ultrasonic wave;

at least one ultrasonic wave is applied to the water;

the turbidity in the water is remeasured (via reflectance measurements) after the application of the ultrasonic wave(s); and the difference in the turbidity is used for determining the concentration of the Calcium/Magnesium/Total Hardness in the water.

Figure 7:
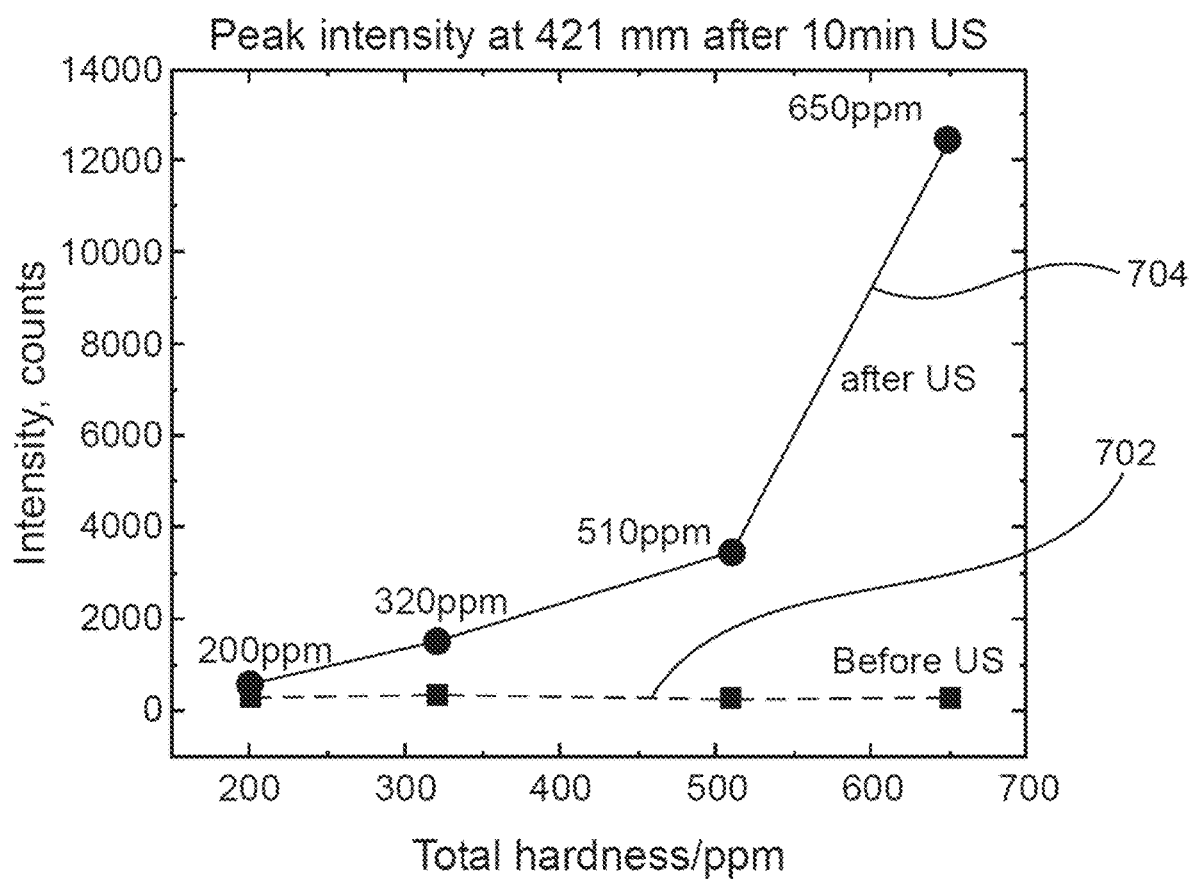
FIG. 7 illustrates curves used for determining the total hardness in the water medium according to some embodiments of the present invention.

FIG. 7 illustrates curves used for determining the total hardness in the water medium according to some embodiments of the present invention.

Curves 702 and 704 correlate the turbidity intensity to the total hardness level prior to and at the end of 10 minutes of ultrasonic application respectively.

Measuring the Bacteria/Particles in the Aqueous Media in the Cuvette:

In accordance with some embodiments of the present invention, ultrasound waves are used for moving bacteria/impurity particles scattered in the water medium towards an optical measurement axis in order to increase the quality of a fundamental investigation of the particles present in the water medium (see FIGS. 8A-C below).

In accordance with some embodiments of the present invention, at least one of the transducers in cuvettes 200A and 200B is used to generate standing ultrasonic waves to focus/concentrate particles and bacteria of various sizes along to the optical path of the cuvette. The particles are centered along the optical measurement axis, and the concentration of the particles in water is measured via spectrometer 118.

Figure 8A:
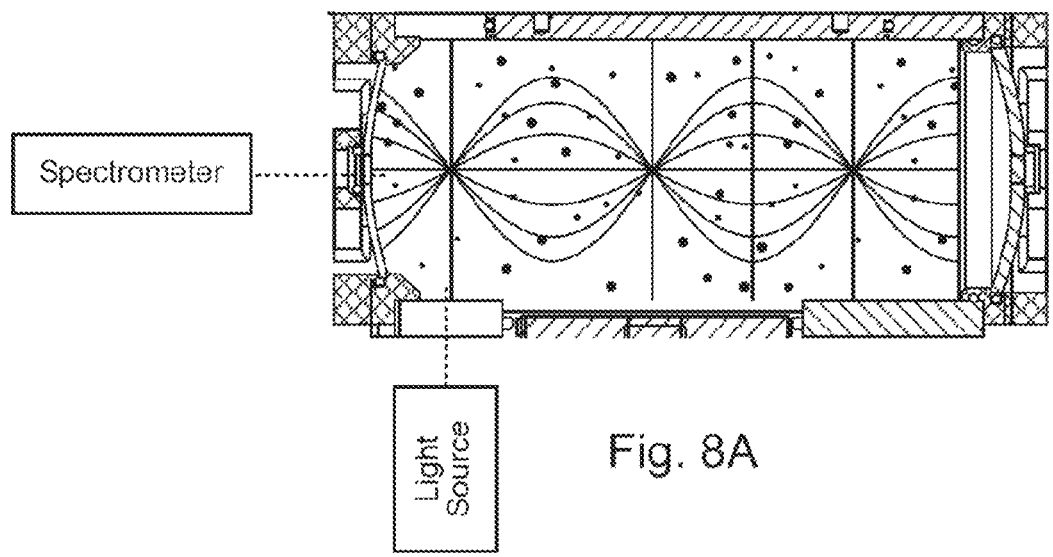
FIGS. 8A-C illustrate particles scattered in a water medium.
Figure 8B:
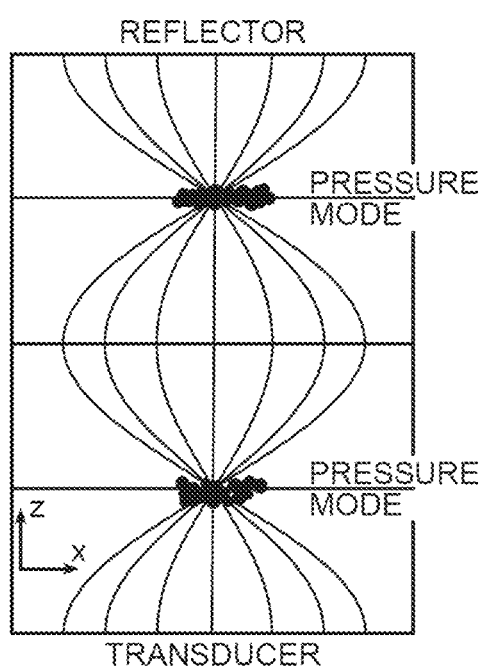
Figure 8C:
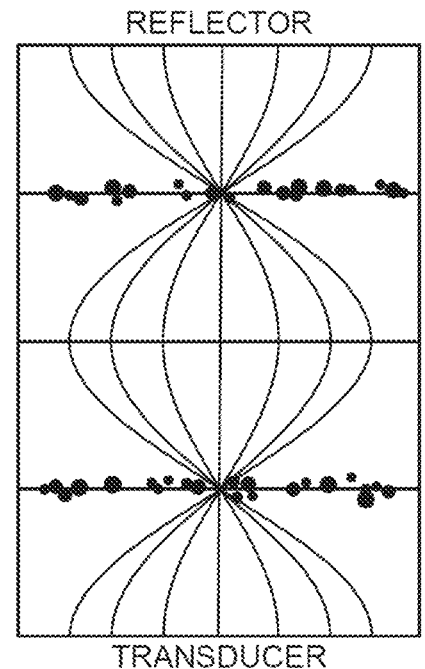

FIGS. 8A-C illustrate particles scattered in a water medium.

FIG. 8A illustrates random scattering of the particles prior to acoustic treatment, FIG. 8B illustrates particles positioned along an optical measurement axis after an ultrasonic treatment, and FIG. 8C illustrates particles centered at an optical measurement axis sometime, shorty (few seconds) after the ultrasonic treatment.

In accordance with some embodiments of the present invention, the light reflected from the various particles is characterized by different wavelengths, and a spectrometric graph is used for determining the content of the water.

In accordance with some embodiments of the present invention, distinguishing between particles and bacteria is enabled as follows:

the reflectance/turbidity and the fluorescence spectrum of the water are measured prior to the application of ultrasonic wave;

at least one ultrasonic wave is applied to the water;

the reflectance/turbidity and the fluorescence of the water are remeasured after the application of the ultrasonic wave(s);

the difference in the reflectance/turbidity is used for determining the concentration of particles in the water; and the difference in the fluorescence spectrum is used for determining the concentration of the bacteria in the water.

In accordance with some embodiments of the present invention, the following 3 parameters should be considered when trying to center particles at the optical measurement axis and in order to produce a spectral measurement that is highly accurate.

the frequency of the ultrasound wave;

the time it takes to center the particles along the optical measurement axis (tens of seconds to seconds)

the intensity and frequency of the ultrasound waves—the intensity and frequency of the ultrasound waves should be kept lower than the intensity and frequency of ultrasound waves associated with cavitation.

Figure 9A:
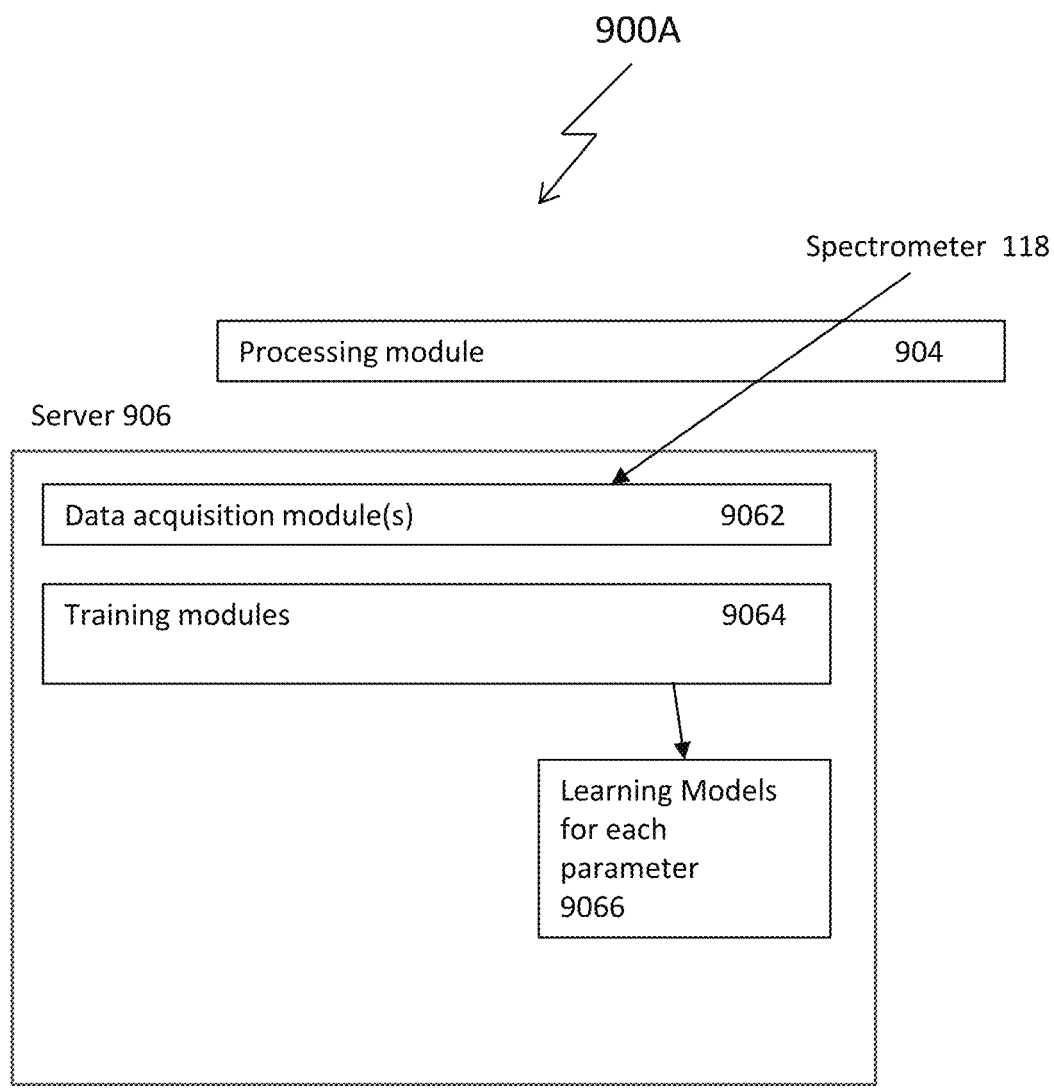
FIGS. 9A&B are block diagrams, depicting an overview of a computing system of cuvette-based system in accordance with some embodiments of the present invention.
Figure 9B:
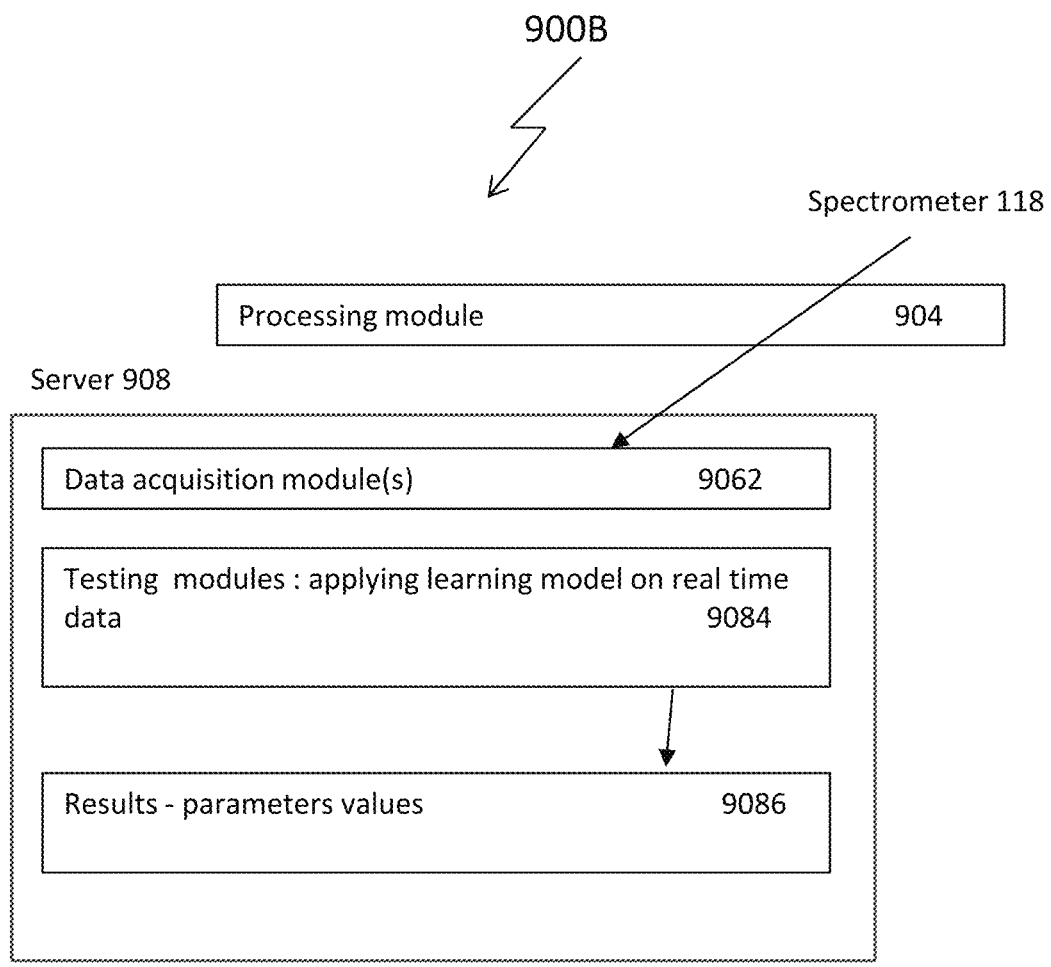

FIGS. 9A&B are block diagrams, depicting an overview of a computing system 900A&B of cuvette-based system 100 in accordance with some embodiments of the present invention.

The computing system 900A&B comprises machine learning algorithms for analyzing multiple light measures that are conducted prior to and after treating the water with ultrasound wave(s). Such light measures include an absorbance spectrum, fluorescence spectrum, reflectance spectrum and more.

As seen in the figures, the computing system 900A&B comprises data acquisition module(s) 9062, training modules 9064, testing modules 9084, learning models 9066, and results—parameters values 9086. Also seen in the figure is spectrometer 118 Which is associated with computing system 900A&B via wired communication or wireless communication.

According to some embodiments of the present invention, the computing system 900A&B analyses changes in light measures as a result of ultrasound wave(s) and the analysis serves as a feedback for the process of training and calibration of the algorithms.

In accordance with some embodiments of the present invention, the data acquisition module(s) 9062 accumulates real-time data and stores it in a database for further processing, said data including at least one of:

light absorbance measurements prior to and after treating the water with ultrasound wave(s);

light reflectance/turbidity measurements prior to and after treating the water with ultrasound wave(s); and fluorescence measurements prior to and after treating the water with ultrasound wave(s).

In accordance with some embodiments of the present invention, the training modules 9064 are comprised of at least one of the following modules:

pH training module 9064A,
free chlorine training module 9064B,
combined chlorine training module 9064C,
calcium/total hardness training module 9064D,
bacteria training module 9064E,
the onset of cavitation training module 9064F,
temperature training module 9064G, and
flow rate training module 9064H.

The training modules 9064 analyse changes induced via ultrasound wave(s) in each one of the above light measures and create multiple learning models—a single model per each parameter, for instance, a learning model for determining the pH,
a learning model for determining the concentration of free chlorine,
a learning model for determining the concentration of combined chlorine,
a learning model for determining the concentration of bacteria,
a learning model for determining the concentration of Calcium/Total Hardness in the water,
a learning model for detecting the onset of cavitation, its duration, bubble size, intensity, etc,
a learning model for determining the temperature of the water, and
a learning model for determining the flow rate in the water.

In accordance with some embodiments of the present invention, the testing modules 9084 apply the learning models 9066 on real time data to determine the pH, the concentration of free chlorine, the concentration of combined chlorine, the concentration of bacteria, the Calcium/Total Hardness in the water, the temperature and/or the flow rate in the water and/or the onset of cavitation, its duration, bubble size, intensity, etc.

FIG. 10 is a flow diagram depicting the functionality of training modules 9064 according to some embodiments of the present invention.

The training modules 9064 reside within the server 906 and are responsible for training or calibrating a machine learning and/or rule based algorithm as follows:

the value of a parameter in the tested water (such as, for instance, pH) is acquired [9100];
a light measure in the tested water (such as absorbance) is acquired prior to generating at least one ultrasonic wave [9200];
at least one ultrasonic wave characterized by an amplitude and frequency suitable for varying the parameter in the water is generated [9300];
measurements of the light measure (such as absorbance) are acquired at the end of the generated at least one ultrasonic wave [9400];
the value of the parameters is acquired at the end of the generated at least one ultrasonic wave [9500]; and
based on accumulated data, a learning model, such as, for instance, a chemometric model, is created for each one of the parameters—the machine learning is trained to create a learning model for each parameter [9600].

FIG. 11 is a flow diagram depicting the functionality of testing modules 9084 according to some embodiments of the present invention.

The testing modules 9084 reside within the server 906 and are responsible for using the learning Models 9066 of the above-mentioned parameters for testing real time data and determining the value of said parameters.

The testing modules 9084 are responsible for testing real time data as follows:

a light measure in the tested water (such as absorbance) is acquired prior to generating at least one ultrasonic wave [9700],
at least one ultrasonic wave is generated [9800]. The ultrasonic wave is characterized by an amplitude and frequency suitable for varying a selected parameter in the water,
measurements (such as absorbance measurements) are acquired after the generation of the at least one ultrasonic wave [9900], and
the learning models 9066 are applied for determining the value of the selected parameter [9950].

Figure 12:
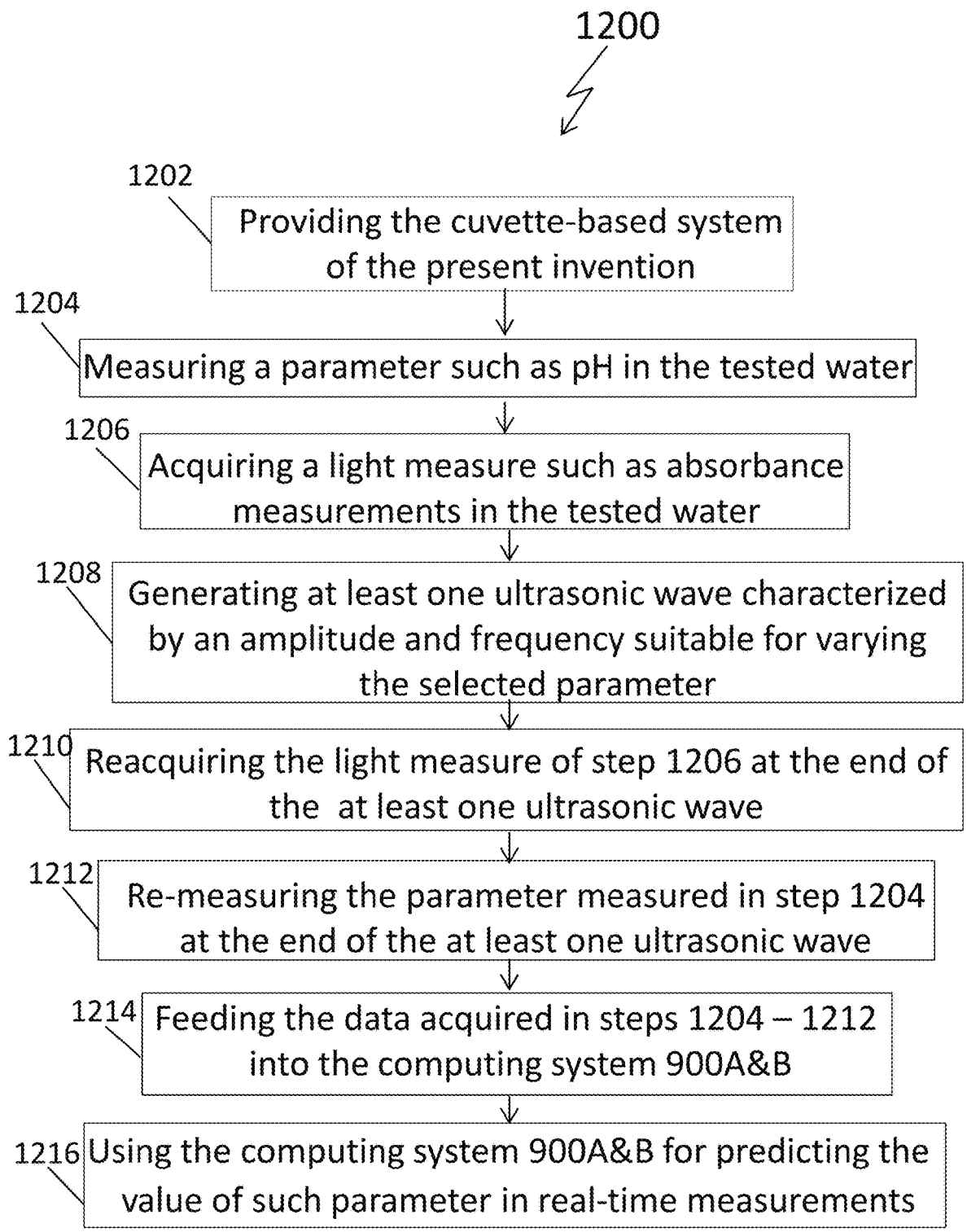
FIG. 12 illustrates a method for treating and characterizing water via ultrasonic waves and optical measurements respectively.

FIG. 12 illustrates a method 1200 for treating and characterizing water via ultrasonic waves and optical measurements respectively.

The method 1200 comprises the following steps:

Step 1202—Providing the cuvette-based system of the present invention;
Step 1204—Measuring a parameter such as pH in the tested water;
Step 1206—Acquiring a light measure (such as absorbance for determining the pH) of the tested water prior to generating at least one ultrasonic wave;
Step 1208—Generating at least one ultrasonic wave characterized by an amplitude and frequency suitable for varying the selected parameter;
Step 1210—Reacquiring the light measure of step 1206 at the end of the at least one ultrasonic wave;
Step 1212—Remeasuring the parameter measured in step 1204 at the end of the at least one ultrasonic wave;
Step 1214—Feeding the data acquired in steps 1204—1212 into the computing system 900A&B; and
Step 1216—Using the computing system 900A&B for predicting the value of such parameter in real-time measurements.

The system of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may wherever suitable operate on signals representative of physical objects or substances.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of a computer or computing system, or processor or similar electronic computing device, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, computing system, communication devices, processors (e.g. digital signal processor (DSP), microcontrollers, field programmable gate array (FPGA), application specific integrated circuit (ASIC), etc.) and other electronic computing devices.

The present invention may be described, merely for clarity, in terms of terminology specific to particular programming languages, operating systems, browsers, system versions, individual products, and the like. It will be appreciated that this terminology is intended to convey general principles of operation clearly and briefly, by way of example, and is not intended to limit the scope of the invention to any particular programming language, operating system, browser, system version, or individual product.

It is appreciated that software components of the present invention including programs and data may, if desired, be implemented in ROM (read only memory) form including CD-ROMs, EPROMs and EEPROMs, or may be stored in any other suitable typically non-transitory computer-readable medium such as but not limited to disks of various kinds, cards of various kinds and RAMs. Components described herein as software may, alternatively, be implemented wholly or partly in hardware, if desired, using conventional techniques. Conversely, components described herein as hardware may, alternatively, be implemented wholly or partly in software, if desired, using conventional techniques.

Included in the scope of the present invention, inter alia, are electromagnetic signals carrying computer-readable instructions for performing any or all of the steps of any of the methods shown and described herein, in any suitable order; machine-readable instructions for performing any or all of the steps of any of the methods shown and described herein, in any suitable order; program storage devices readable by machine, tangibly embodying a program of instructions executable by the machine to perform any or all of the steps of any of the methods shown and described herein, in any suitable order; a computer program product comprising a computer useable medium having computer readable program code, such as executable code, having embodied therein, and/or including computer readable program code for performing, any or all of the steps of any of the methods shown and described herein, in any suitable order; any technical effects brought about by any or all of the steps of any of the methods shown and described herein, when performed in any suitable order; any suitable apparatus or device or combination of such, programmed to perform, alone or in combination, any or all of the steps of any of the methods shown and described herein, in any suitable order; electronic devices each including a processor and a cooperating input device and/or output device and operative to perform in software any steps shown and described herein; information storage devices or physical records, such as disks or hard drives, causing a computer or other device to be configured so as to carry out any or all of the steps of any of the methods shown and described herein, in any suitable order; a program pre-stored e.g. in memory or on an information network such as the Internet, before or after being downloaded, which embodies any or all of the steps of any of the methods shown and described herein, in any suitable order, and the method of uploading or downloading such, and a system including server/s and/or client/s for using such; and hardware which performs any or all of the steps of any of the methods shown and described herein, in any suitable order, either alone or in conjunction with software. Any computer-readable or machine-readable media described herein is intended to include non-transitory computer- or machine-readable media.

Any computations or other forms of analysis described herein may be performed by a suitable computerized method. Any step described herein may be computer-implemented. The invention shown and described herein may include (a) using a computerized method to identify a solution to any of the problems or for any of the objectives described herein, the solution optionally include at least one of a decision, an action, a product, a service or any other information described herein that impacts, in a positive manner, a problem or objectives described herein; and (b) outputting the solution.

The scope of the present invention is not limited to structures and functions specifically described herein and is also intended to include devices which have the capacity to yield a structure, or perform a function, described herein, such that even though users of the device may not use the capacity, they are, if they so desire, able to modify the device to obtain the structure or function.

Features of the present invention which are described in the context of separate embodiments may also be provided in combination in a single embodiment.

For example, a system embodiment is intended to include a corresponding process embodiment. Also, each system embodiment is intended to include a server-centered "view" or client centered "view", or "view" from any other node of the system, of the entire functionality of the system, computer-readable medium, apparatus, including only those functionalities performed at that server or client or node.

The invention claimed is:

1. A cuvette-based system for treating and characterizing water, the system comprising:
 a cuvette configured for holding water therein;
 at least one ultrasonic transducer for the water in the cuvette by introducing ultrasonic waves into the water in the cuvette;
 at least one light source configured and located such as to irradiate said water in the cuvette; and
 a spectrometry device for measuring spectral characteristics of output light outputted from the cuvette prior to and after the treating of the water; and
  a processing unit, configured to receive data from the spectrometry device indicative of spectral characteristics of the output light before and after the ultrasonic treatment of the water in the cuvette and determine, based on the received data, value of at least one parameter indicative of the effect to the water in the cuvette caused by the treatment by the ultrasonic signals,
 wherein the value of the at least one parameter of the water is determined by:
 (a) measuring the spectral characteristics of the output light prior to treating the water with the ultrasonic waves;
 (b) treating the water with the ultrasonic waves;
 (c) re-measuring the spectral characteristics of the output light;

(d) determining the differences between corresponding spectral characteristics of the output light measured before and after the ultrasonic treatment; and
(d) determining the value of the at least one parameter of the water based on the differences in said spectral characteristics of the output light.

2. The cuvette-based system of claim 1, wherein said at least one light source is arranged at a 90-degree angle to the spectrometry device, or at a 180-degree angle to the spectrometry device.

3. The cuvette-based system of claim 1, wherein said at least one transducer comprises at least one low frequency ultrasonic transducer and/or at least one spherical transducer.

4. The cuvette-based system of claim 3, wherein said at least one ultrasonic transducer generates ultrasonic waves, characterized by an amplitude and frequency suitable for causing cavitation in the water, thereby causing changes in physical, chemical and/or spectral characteristics of the water.

5. The cuvette-based system of claim 1, wherein said at least one parameter is selected from pH, quantity and/or concentration of: free chlorine, combined chlorine, calcium, Magnesium, bacteria, and/or total water hardness, water flow rate, and/or water temperature.

6. The cuvette-based system of claim 1, wherein each of said at least one ultrasonic transducer is connected to a pulser, a receiver and/or a pulse generator.

7. The system of claim 1, wherein said at least one ultrasonic transducer comprises a sensor having a frequency range of 20-120 KHZ.

8. The cuvette-based system of claim 1, wherein the at least one parameter is indicative of at least one influence caused to the water by the introduction of the ultrasonic treatment to the water, the influence comprising at least repositioning of particles in the water, wherein the repositioning of the particles is influenced by (a) the intensity and/or frequency of the ultrasonic waves, (b) the time required to center the particles along an optical measurement axis.

9. The cuvette-based system of claim 1 further comprising an online server, configured for accumulating data of determined values of the at least one parameter from said processing unit, applying one or more machine learning algorithms, using the accumulated data and determining values of measured parameters of said water,
wherein said one or more machine learning algorithms comprising at least one learning model trained to learn the behavior of said accumulated data and to provide values of parameters of said water.

10. The cuvette-based system of claim 1, wherein the one or more characteristics of the influence of the ultrasonic treatment to the water indicated by the at least one parameter value comprise changes in one or more of: water turbidity level, water fluorescence characteristics, water scattering characteristics, water reflectivity characteristics.

11. The cuvette-based system of claim 10, wherein changes in fluorescence optical characteristics of the output light is indicative of changes in concentration of microbiology in the sampled water.

12. The cuvette-based system of claim 1, wherein said processing unit is further configured to record the time and date at which each one of said measurements is performed.

13. The cuvette-based system of claim 1, further comprising:
a liquid splitter,
a De-bubbler system,
a cooling system, and
a liquid combiner,
wherein when said water enters said cuvette-based system, it passes into said liquid splitter where it splits into two streams, a first stream and a second stream, the first stream enters into said cooling system for cooling multiple components of said cuvette-based system, and the second stream enters into said De-bubbler to remove bubbles from the water prior to entering into said cuvette, the water exiting from said cuvette recombines with the water exiting from said cooling system in said liquid combiner.

14. The cuvette-based system of claim 13, wherein said first stream enters into said cooling system for cooling at least one of: the first light source, the second light source, and the spectrometer.

15. A method for treating and characterizing water comprising:
(a) providing a cuvette-based system comprising a cuvette holding water therein, at least one ultrasonic transduces for applying ultrasonic waves to the water in the cuvette, a light source for irradiating the cuvette and a spectrometry device for detecting spectral characteristics of output light, outputted from the cuvette;
(b) measuring spectral characteristics of output light outputted from the cuvette prior to treating the water therein with said ultrasonic waves;
(c) treating the water in the cuvette with ultrasonic waves, using the at least one ultrasonic transducer;
(d) re-measuring the spectral characteristics of output light outputted from the cuvette, and
(e) determining the differences between spectral characteristics of the output light measured before and after the ultrasonic treatment;
(f) determining the value of the at least one parameter of the water based on the difference in said spectral characteristics of output light,
(g) accumulating data from said spectrometry device, and
(h) using one or more machine learning models trained to learn the behavior of said data acquired from said spectrometry device and to provide values of parameters of said water.

16. The method of claim 15, wherein said at least one parameter is selected from: pH, total water hardness, water flow rate, water temperature, concentration of one or more of: free chlorine, combined chlorine, bacteria, calcium, magnesium.

17. The method of claim 15 further comprising determining the total water hardness in the water via the difference in the reflectance and/or turbidity of output light before and after the ultrasonic treatment.

18. The method of claim 15 further comprising determining the concentration of microbiology in the water via the difference in characteristics of the output light, before and after the ultrasonic treatment.

* * * * *